(12) United States Patent
Howard (10) Patent No.: US 10,034,810 B1
(45) Date of Patent: *Jul. 31, 2018

(54) APPARATUS AND METHOD FOR APPLYING SPINAL TRACTION FORCE

(71) Applicant: John V. Howard, Cumming, GA (US)

(72) Inventor: John V. Howard, Cumming, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/359,042

(22) Filed: Nov. 22, 2016

Related U.S. Application Data (63) Continuation of application No. 14/644,646, filed on Mar. 11, 2015, now Pat. No. 9,498,367.

(51) Int. Cl.
*A61H 1/02* (2006.01)
*A61F 5/042* (2006.01)

(52) U.S. Cl.
CPC ........... *A61H 1/0229* (2013.01); *A61F 5/042* (2013.01); *A61H 1/0292* (2013.01); *A61H 2201/0115* (2013.01); *A61H 2201/0192* (2013.01); *A61H 2201/1215* (2013.01); *A61H 2201/14* (2013.01); *A61H 2203/02* (2013.01)

(58) Field of Classification Search
CPC .. A61H 1/0218; A61H 1/0292; A61H 1/0229; A61H 2201/1607; A61H 2203/0493; A61H 2201/1642; A61F 5/04; A63B 23/0211; A63B 23/0233
See application file for complete search history.

(56) References Cited

U.S. PATENT DOCUMENTS

| | | |
|---|---|---|
| 3,134,379 A | 5/1964 | Nightingale |
| 3,593,708 A | 7/1971 | Steele |
| 3,960,146 A | 6/1976 | Albrecht |
| 5,020,520 A | 6/1991 | Lawlis |
| 5,040,523 A | 8/1991 | Wu |
| 5,052,378 A | 10/1991 | Chitwood |
| 5,637,079 A | 6/1997 | Miller |
| 5,774,916 A | 7/1998 | Kurhi |
| 6,045,525 A | 4/2000 | Chitwood |
| 6,113,564 A | 9/2000 | McGuire |

(Continued)

FOREIGN PATENT DOCUMENTS

| | | |
|---|---|---|
| EP | 87303977.0 A2 | 11/1987 |
| WO | WO 96/14810 A2 | 5/1996 |

OTHER PUBLICATIONS

Amendment filed May 19, 2016 in U.S. Appl. No. 14/644,646.

(Continued)

*Primary Examiner* — Ophelia A Hawthorne
(74) *Attorney, Agent, or Firm* — James E. Walton (57) ABSTRACT

An apparatus for applying traction force to a spine of a user has a chassis with an upper surface. A user lies on the upper surface with the spine extending generally parallel to a longitudinal axis of the chassis. Two members extend from the chassis on opposing sides of the longitudinal axis, each member being positioned to engage an armpit. A lever is pivotally attached to the chassis for rotation about a lateral axis, and a pad coupled to the lever contacts a proximal portion of each upper leg when the leg is bent forward at a hip joint. A force applied to the lever is transmitted through the pad to each upper leg and opposed by the members, thereby applying traction force for decompressing the spine. The force may be applied by the arms of the user or by a motor.

20 Claims, 9 Drawing Sheets

(56) References Cited

U.S. PATENT DOCUMENTS

| | | |
|---|---|---|
| 6,315,750 B1 | 11/2001 | Gray |
| 6,506,174 B1 | 1/2003 | Saunders |
| 6,533,743 B1 | 3/2003 | Moss |
| 6,811,522 B1 | 11/2004 | McQuinn |
| 6,994,683 B1 | 2/2006 | Starr |
| 8,535,254 B2 | 9/2013 | Gazayerli |
| 8,652,081 B2 | 2/2014 | Rawlings |
| 9,498,367 B1 * | 11/2016 | Howard ................. A61F 5/042 |
| 2005/0273140 A1 | 12/2005 | Boghosian |

OTHER PUBLICATIONS

Office Action dated Mar. 9, 2016 in U.S. Appl. No. 14/644,646.
Notice of Allowance dated Sep. 30, 2016 in U.S. Appl. No. 14/644,646.

\* cited by examiner

APPARATUS AND METHOD FOR APPLYING SPINAL TRACTION FORCE

This application is a continuation of U.S. Utility patent application Ser. No. 14/644,646 filed Mar. 11, 2015, now U.S. Pat. No. 9,498,367.

BACKGROUND

1. Field of the Invention

The present application relates in general to spinal traction devices and in particular to devices utilizing force applied by the user through a lever or by a motor to apply high traction loads.

2. Description of Related Art

A significant number of devices exist for applying traction force to the human body, and these are often intended to relieve back or leg pain commonly experienced by those with spinal problems. Spinal traction is a decompression therapy, and the goal is to relieve pressure on compressed discs. Traction may be used to treat herniated discs, sciatica, degenerative disc disease, pinched nerves, and many other back conditions. Spinal traction is claimed to increase the intervertebral space, cause tension of the posterior longitudinal vertebral ligament, and cause suction to draw any disc protrusion towards the center of the joint.

Common devices for applying traction include inversion tables, gravity boots and other more complex devices, such as two-part tables. Devices such as gravity boots and inversion tables rely on the suspended weight of the user's upper torso to provide traction forces on the lower spine. These forces may be no greater than 90 lbs at the base of the spine, reducing linearly to the suspended weight of the user's head at the second thoracic vertebra (T2) in the upper spine, which may result in less than 20 lbs of force.

Figure 1:
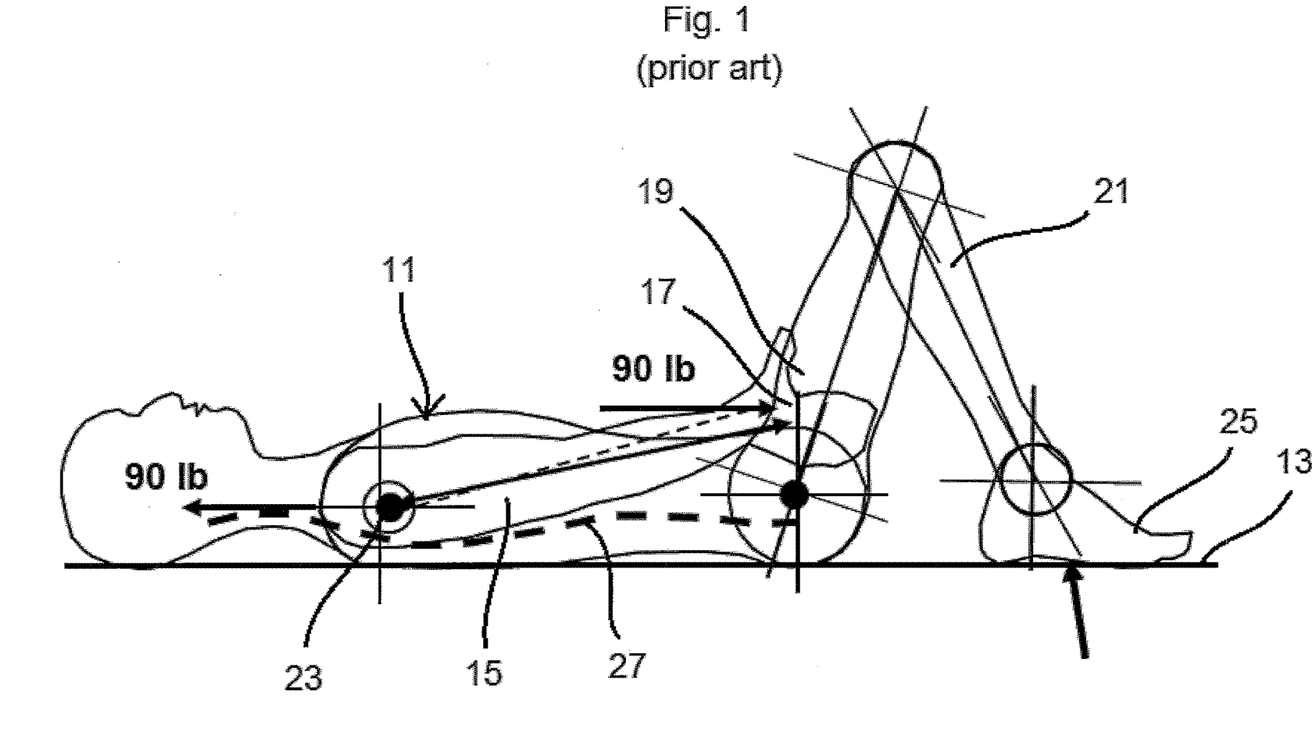
FIG. 1 is a schematic side view of a person performing an exercise according to the prior art.

An exercise for spinal decompression, shown in FIG. 1, involves a person 11 lying on a surface 13 and using arms 15 to supply a force for spinal decompression. Person 11 extends arms 15 and forces hands 17 onto a proximal, or upper, portion 19 of bent legs 21. The force is reacted, or opposed, by shoulder joints 23 and feet 25, which are resting on surface 13. A force of about 50 lb applied by each arm 15 results in approximately 90 lb of spinal traction force on spine 27. This is approximately equal to the force applied by the existing devices described above, but an advantage of this exercise over gravity boots and inversion tables is that the force does not vary along most of the length of spine 27.

Although great strides have been made in spinal traction devices, considerable shortcomings remain.

DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

The numbers adjacent the small arrows represent applied loads. The numbers in boxes connected to small arrows represent horizontal loads on the body. The number in boxes connected to wide arrows represent weight of body part. While the apparatus and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms to describe a spatial relationship between various components or to describe the spatial orientation of aspects of such components should be understood to describe a relative relationship between the components or a spatial orientation of aspects of such components, respectively, as the device described herein may be oriented in any desired direction.

There is a need for a simple, inexpensive, and portable spinal traction device capable of applying traction loads that are significantly higher than those obtained by current devices. Additionally, there is a need for a spinal traction device that is simple to use and provides an easy and convenient way to apply these higher traction forces. A method has been devised allowing a user to selectively apply a force to the upper part of the inclined femur and react this force in the armpits of the user. The force may be supplied by a lever operated by the user's arms or by an electric motor. By leveraging the arm load it is possible to apply a significantly higher traction load throughout most of the spine than can be achieved by most existing devices.

Most spinal traction therapy is performed at or below the level of 90 lb of force, likely due to the fact that most devices are unable to exceed this level. There is some evidence that greater benefit can be obtained with higher load, and medical literature shows that force levels up to 250 lb have been well tolerated. However, care must be taken not to overload the spine, because damage can occur at loads of 550 lb or greater. In this respect, the apparatus according to the present application is self-limiting, as the degree of discomfort the user feels will limit the load level being applied.

A method and apparatus are herein disclosed that allow spinal traction loads to reach three times the load levels typically obtained by gravity boot inversion tables or other much more complicated devices. In addition, the traction remains constant throughout most of the length of the spine and is applied while the user remains in a comfortable, non-inclined, non-inverted orientation. To achieve high traction loads, one embodiment of the apparatus employs a novel means of leveraging the power applied directly by the user. The user can also control both the duration and level of the traction load. Also the configuration is arranged so that easy adjustments can be made to fit a range of human sizes, although it may be advantageous to make the main platform in three basic sizes. No larger than a small sled, the apparatus is simple, lightweight, and inexpensive to manufacture. It is readily portable and takes up little storage space for use in confined quarters.

FIGS. 2 through 5 illustrate a preferred embodiment of a spinal traction device 29 according to the present application. Referring to the figures, a sled-like chassis 31 is elongated along a longitudinal axis and preferably formed as a one-piece, injection-molded, plastic body of suitable wall thickness. An upper surface 33 of chassis 31 is preferably smooth so that user 11 can slide longitudinally along surface 33 with a minimum of friction. Surface 33 undulates along its length to accommodate the natural curvature of spine 27. A foot rest 35 is located at a distal end of surface 33, and a pair of abrasive foot pads 37 is provided to locate feet 25 and to provide sufficient friction to prevent them from sliding longitudinally on surface 33.

A pair of rectangular side members 39 is formed on chassis 31, members 39 extending longitudinally and being generally perpendicular to surface 33. Adjustment sliders 41 have a rectangular cross-section corresponding to a proximal open end of members 39, allowing each slider 41 to be received within the open end of one of members 39. Sliders 41 are slidable relative to members 39 for adjusting length to fit user 11, and sliders 41 are retained by pins that engage regularly spaced holes 43 in both sliders 41 and members 39. The proximal end of each slider 41 is appropriately contoured to fit comfortably under the armpit of user 11 and provided with slider pad 45 to ensure maximum comfort for user 11.

A removable load frame 47 is rotatably mounted to chassis 31 at hinge 49, which forms a lateral rotation axis passing through members 39. Frame 47 is generally rectangular and comprises a pair of lever arms 51 connected to each other at an outer end by a padded handlebar 53 and by crossbar 55 at an intermediate location. The inner ends of lever arms 51 are connected to chassis 31 at hinge 49, and arms are preferably formed from a stiff and strong material, such as tubing formed from aluminum or steel. A pair of stiff leg pads 57, which may have a "saddle" shape like those shown, are rotatably attached to crossbar 55. Each leg pad 57 is laterally positioned to engage proximal portion 19 of one of legs 21 of user 11 near hip joint 59. The unequal radii defined by the distance of handlebar 53 and crossbar 55 from hinge 49 create a lever that multiplies force applied at handlebar 53 and transferred through leg pads 57 into proximal portions 19 of legs 21. In the embodiment shown, the leverage ratio is approximately 3:1. A one-way ratchet pawl and release mechanism (not shown) is also provided at hinge 49 so that the load frame 47 can be temporarily locked in the loaded position, thereby freeing hands 17 of user 11. A release button may be located on handlebar 53 for allowing user 11 to unlock load frame 47.

Figure 2:
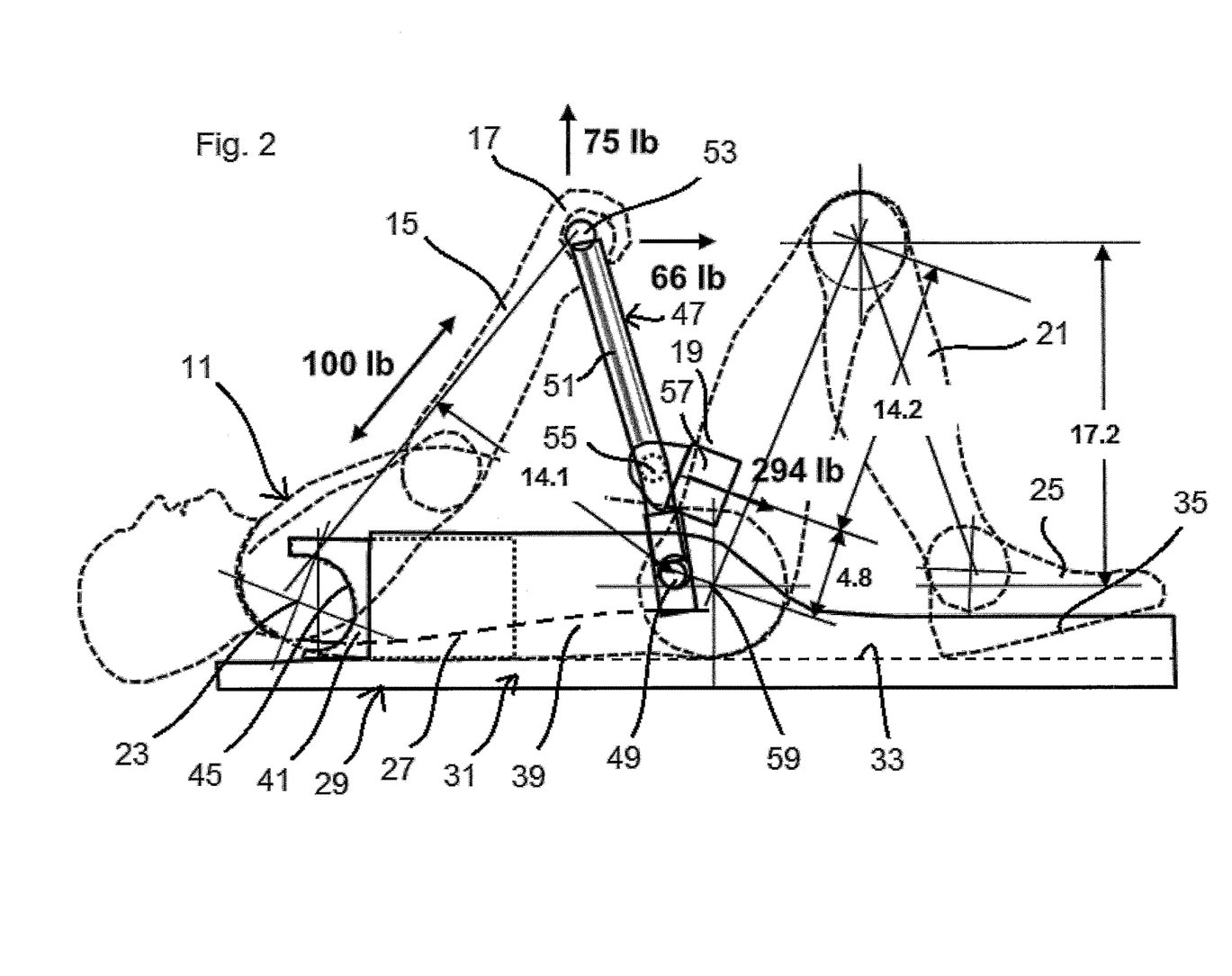
FIG. 2 is a is a schematic side view of a person performing an exercise using an apparatus and method according to the present application.
Figure 3:
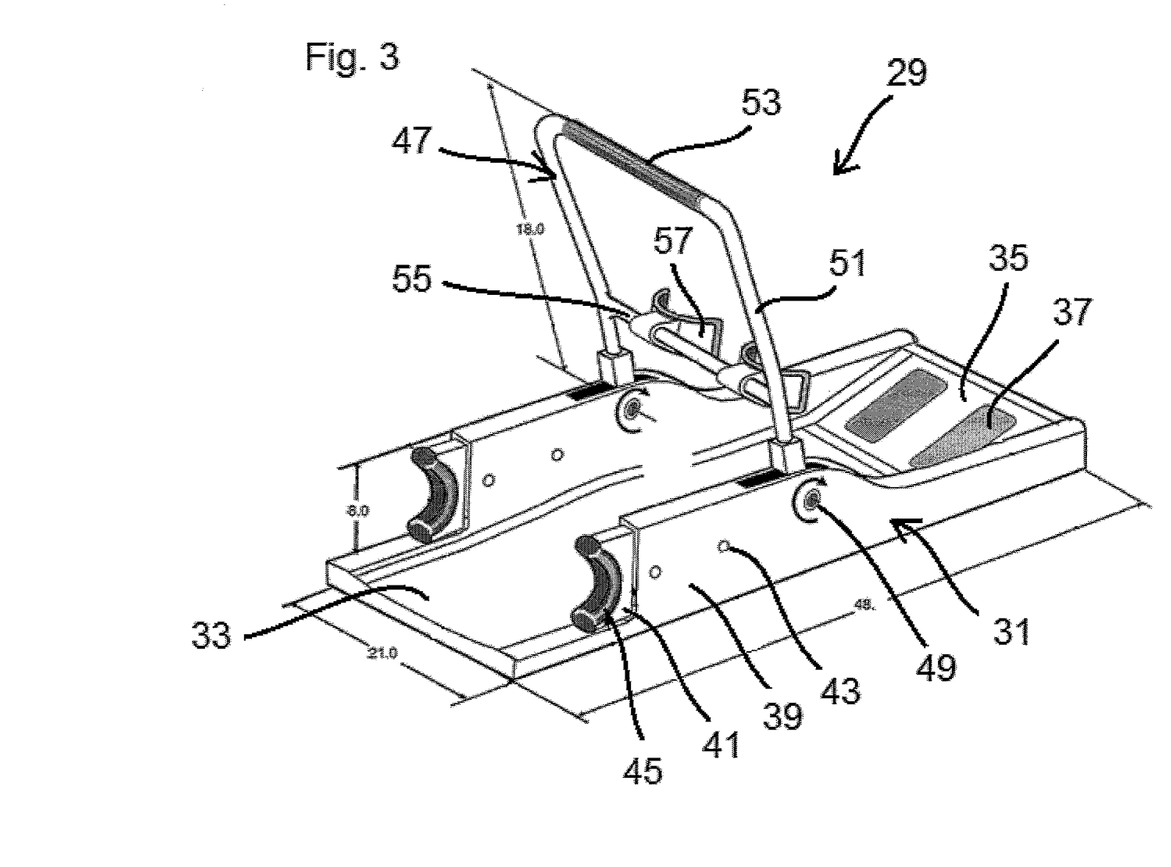
FIG. 3 is an oblique view of the apparatus of FIG. 2.
Figure 4:
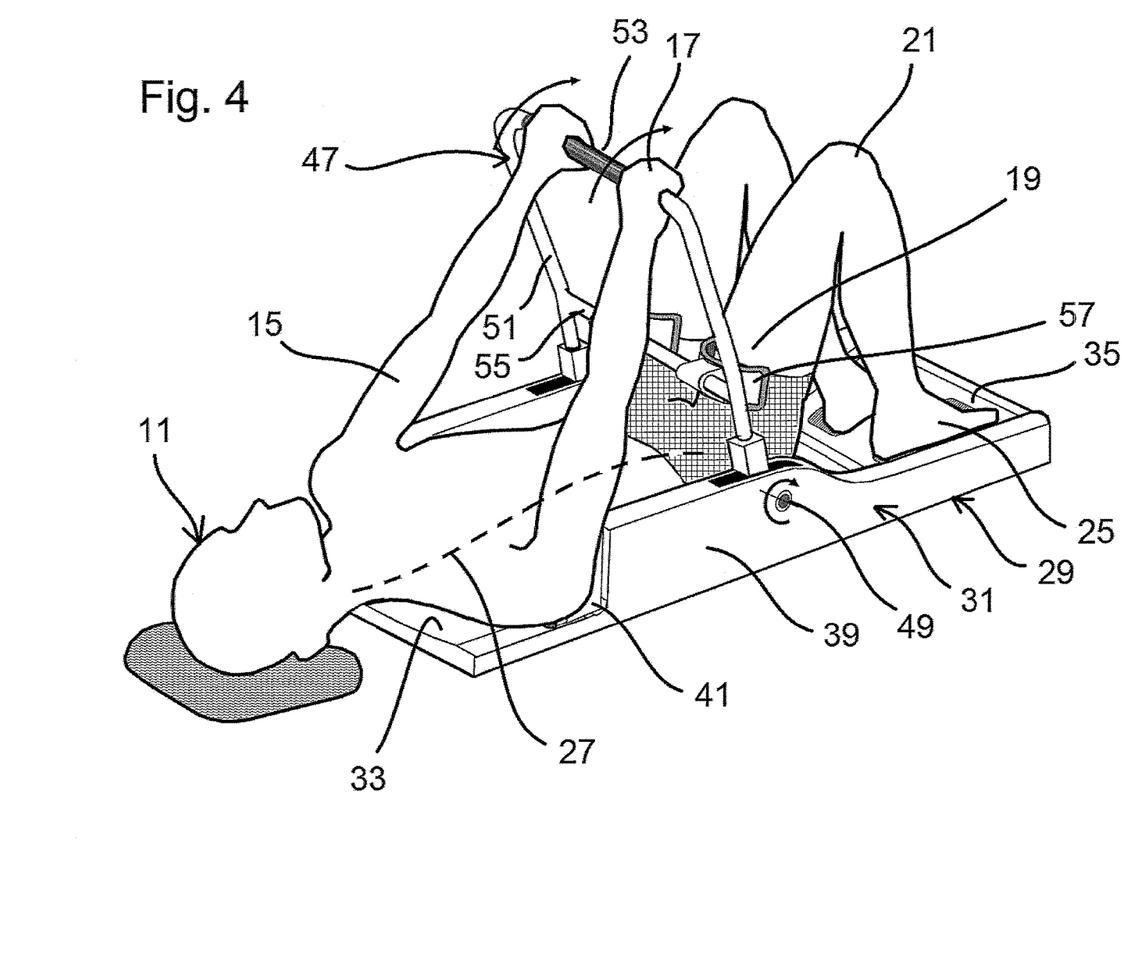
FIG. 4 is an oblique view of a person using the apparatus of FIG. 2.

A shown in FIGS. 2 and 4, during operation of device 29 user 11 lies on chassis 31 with the back of user 11 adjacent surface 33. User 11 may adjust the position of sliders 41 within members 39 to locate slider pads 45 adjacent the armpits of user 11. User 11 bends legs 21 and places feet 25 on foot pads 37 of foot rest 35. User 11 extends arms 15 and grabs handlebar 53 with hands 17, and then user 11 applies force with arms 15. The input force at handlebar 53 is transferred through lever arms 51 to crossbar 55, and an output force is transferred into leg pads 57. Because of the lever configuration of load frame 47, the input force is multiplied by the lever ratio and results in a higher output force being transferred through leg pads 57. This increased force is then transferred into proximal portions 19 of legs 21 and through hip joints 59 into the distal end of spine 27. Though feet 25 react a portion of this force, the majority of the force is applied to hip joints 59, and this tends to move the torso of user 11 longitudinally along surface 33 toward feet 25. However, sliders 41 engage the armpits of user 11 and arms 15 are pressing against handlebar 53, and these cooperate to prevent user 11 from sliding toward feet 25 and react through the armpits and shoulder joints 23 the force applied to legs 21. Thus, the force applied to hip joints 59 and opposed at the armpits and shoulder joints 23 tends to elongate spine 27, providing decompression therapy for user 11. In this manner, the majority of the spine up to vertebra T2 can be loaded up to a level of 240 lb, versus a maximum load of only 90 lb diminishing to about 20 lb at T2 achieved by gravity boots and inversion tables.

Figure 5:
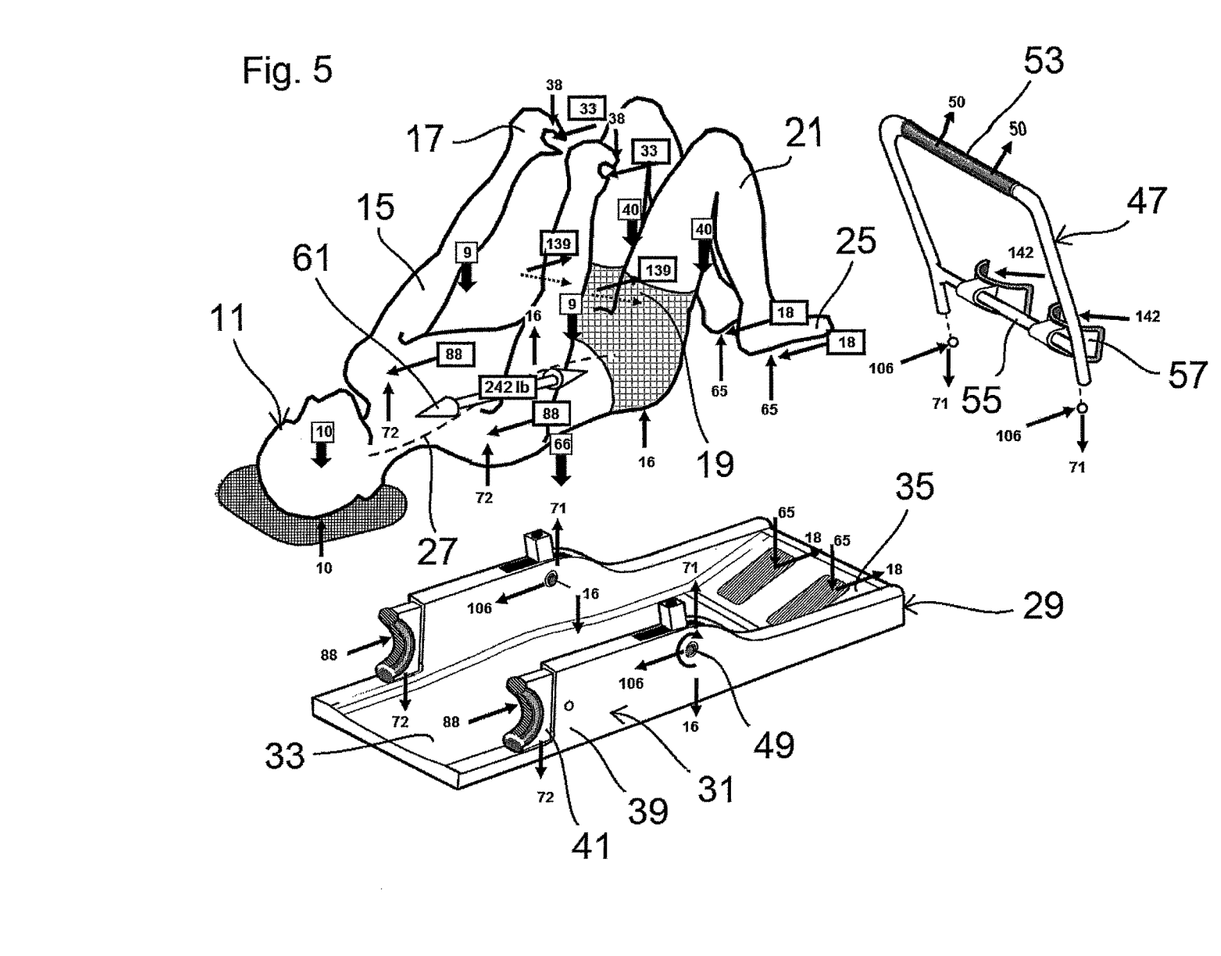
FIG. 5 is an oblique view showing the forces exerted on and by the person and on the components of the apparatus of FIG. 2.

FIGS. 2 and 5 show force values derived from the kinematics of device 29. For example, a longitudinal force of 66 lbs at handlebar 53 (33 lb for each hand 17) results in a spinal traction force of 242 lb, as shown at 61. To achieve a traction force of 90 lb, as achieved in the prior art devices, requires a force of only 12 lb per hand 17. To minimize the chance that user 11 could cause injury by applying excessive force to handlebar 53, it is preferred that a load-limiting device, such as a slip clutch or other torque-limiting device, is installed at hinge 49.

Figure 6:
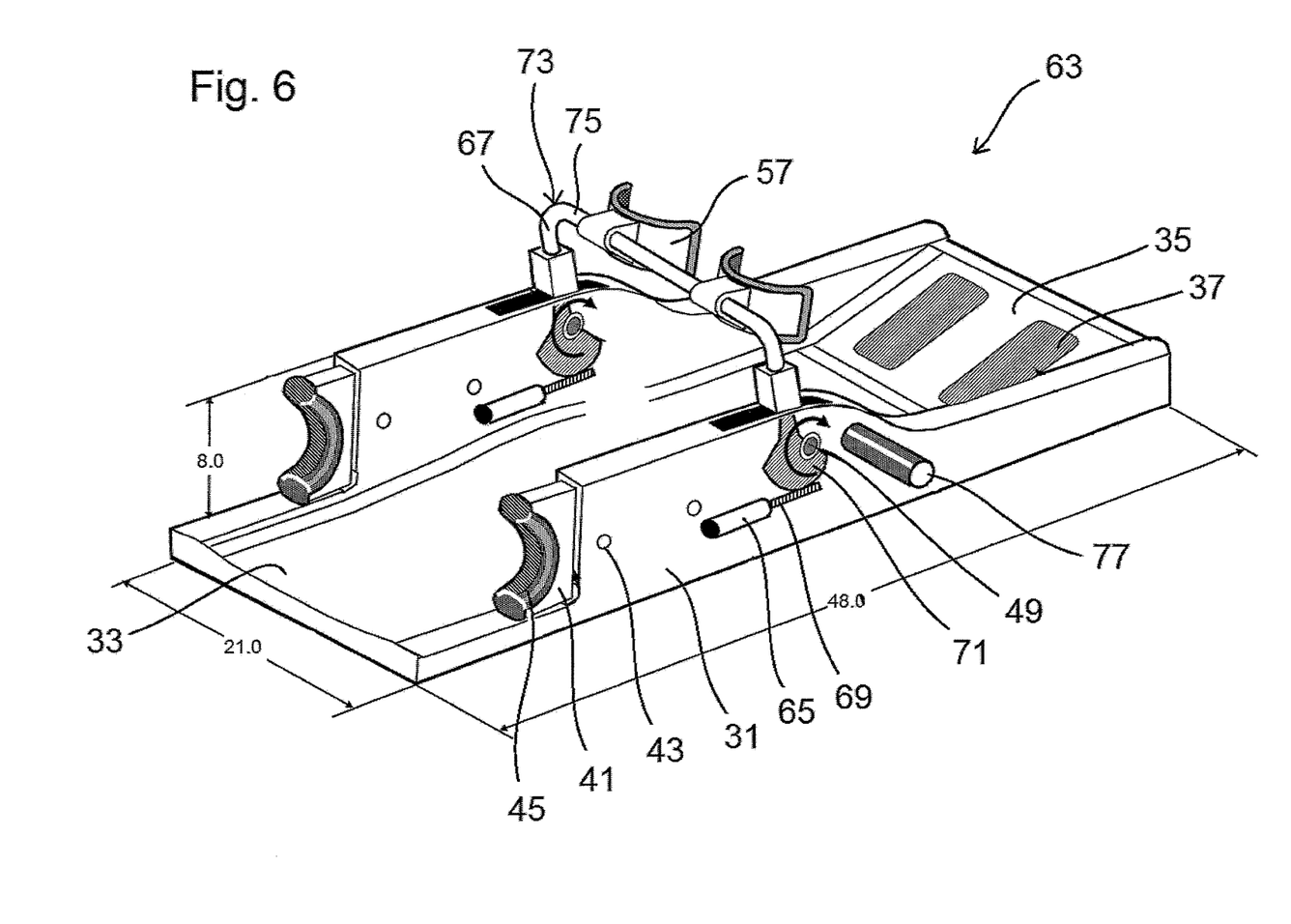
FIG. 6 is an oblique view of an alternative embodiment of an apparatus according to the present application.
Figure 7:
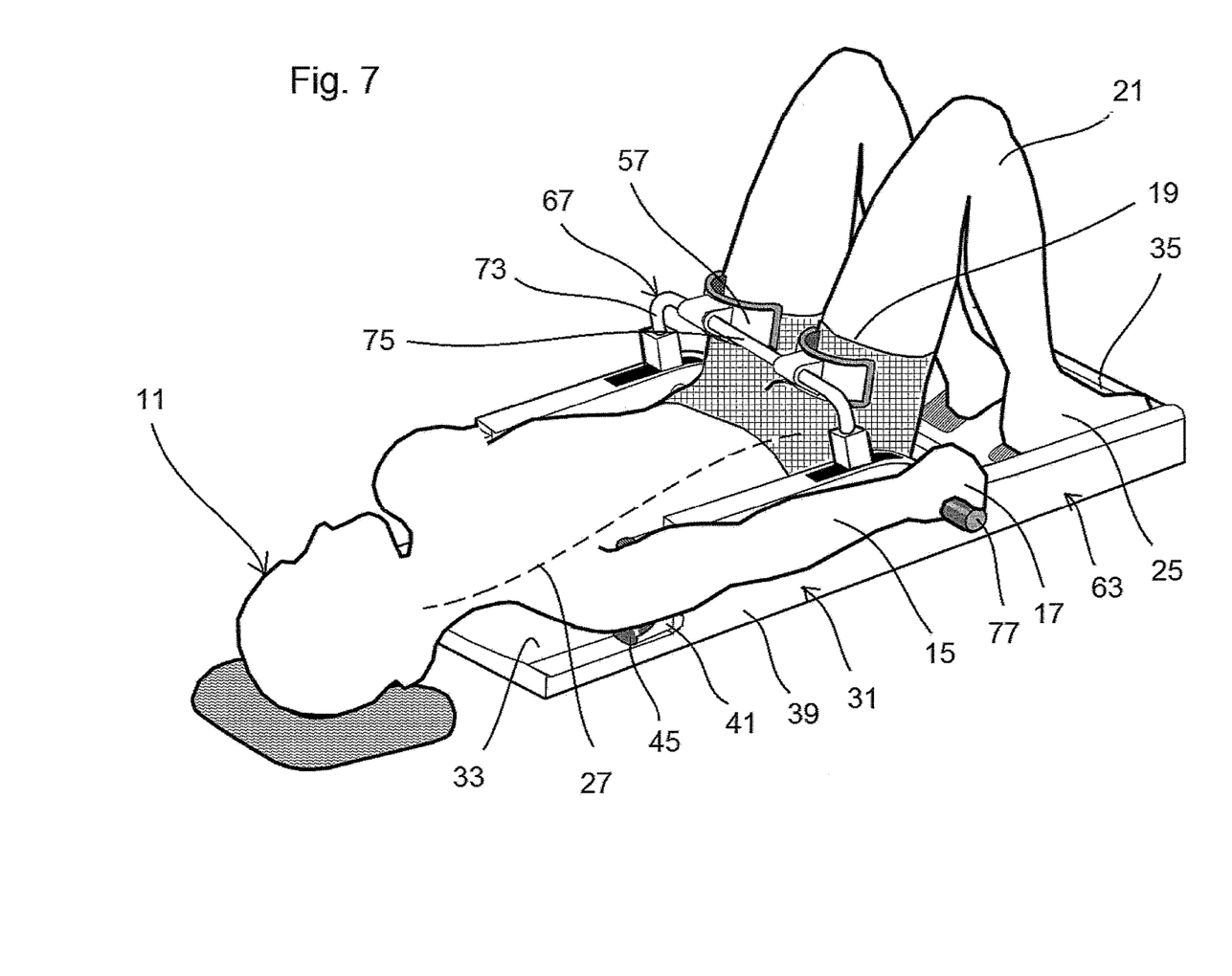
FIG. 7 is an oblique view of a person using the apparatus of FIG. 6.
Figure 8:
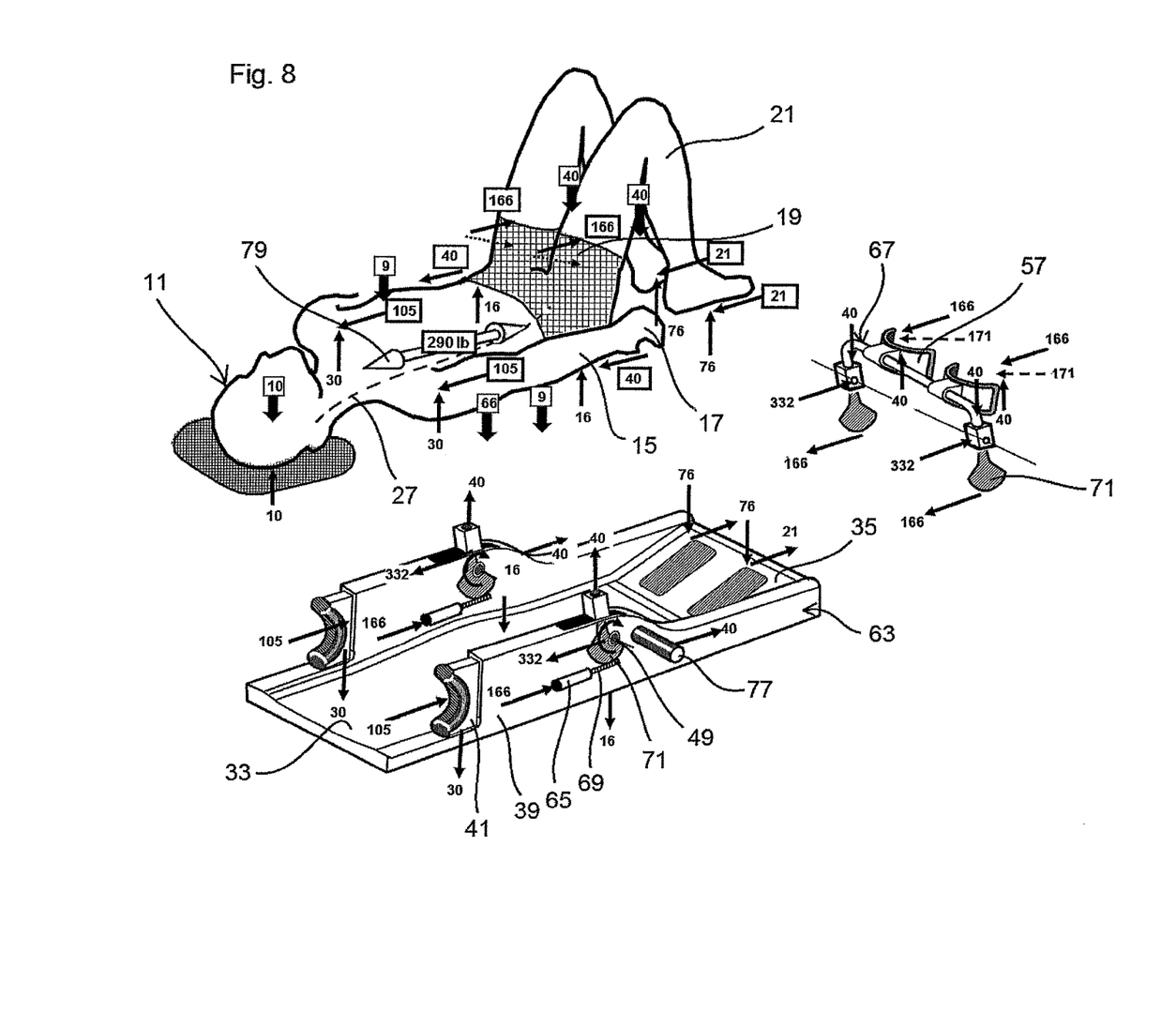
FIG. 8 is an oblique view showing the forces exerted on and by the person and on the components of the apparatus of FIG. 6.

FIGS. 6 through 8 illustrate an alternative embodiment of a spinal traction device 63 according to the present application. Device 63 is constructed similarly to device 29 and comprises similar or identical components. Device 63 comprises a chassis 31 with upper surface 33, foot rest 35 with foot pads 37, and members 39 that receive adjustment sliders 41. However, instead of load frame 47 on which a user applies force with arms 15, device 63 has electric motors 65 provide the force needed to decompress spine 27. Motors 65 are preferably operated using a rechargeable power source (not shown).

A shorter, removable load frame 67 replaces load frame 47 used in device 29. Motors 65 are selectively operated to rotate drive screws 69, which engage gear teeth on quadrants 71. Quadrants 71 are rotatably mounted to chassis 31 at hinge 49. Rotation of each drive screw 69 causes the connected quadrant 71 to rotate about hinge 49, and rotation of drive screws 69 in the opposite direction causes opposite rotation of quadrants 71. Load frame 67 is generally rectangular and comprises a pair of short lever arms 73 connected to each other at an outer end by crossbar 75. The inner end of each lever arm 73 is connected to a corresponding quadrant 71, allowing motors 65 to be operated for causing rotation of load frame 67. Leg pads 57 are rotatably mounted to crossbar 75, and each leg pad 57 is laterally positioned to engage proximal portion 19 of one of legs 21 near hip joint 59. Grips 77 are rotatably mounted on opposing sides of chassis 31 and provide a twisting means for operating motors 65.

FIG. 7 shows device 63 in use by user 11. During operation of device 63 user 11 lies on chassis 31 after adjusting the position of sliders 41 within members 39. User 11 bends legs 21 and places feet 25 on foot pads 37 of foot rest 35. User 11 extends arms 15 and grabs grips 77 with hands 17, and then user 11 operates motors 65 by twisting grips 77. Motors 65 rotate drive screws 69, which causes quadrants 71 to rotate about hinge 49. This causes load frame 67 to rotate in the desired direction. When load frame 67 rotates toward feet 25 and contacts proximal portions 19, force is applied to lever arms 73 and into crossbar 75 and leg pads 57. The force is then transferred into proximal portions 19 of legs 21 and through hip joints 59 into the distal end of spine 27. Feet 25 react a portion of this force, but the majority of the force is applied to hip joints 59. Sliders 41 engage the armpits of user 11 and arms 15 are pressing against grips 77, and these cooperate to prevent user 11 from sliding toward feet 25 and react through the armpits and shoulder joints 23 the force applied to legs 21. Thus, the force applied to hip joints 59 and opposed at the armpits and shoulder joints 23 tends to elongate spine 27, providing decompression therapy for user 11. In this manner, the majority of the spine up to vertebra T2 can be loaded up to a level of 290 lb, versus a maximum load of only 90 lb diminishing to about 20 lb at T2 achieved by gravity boots and inversion tables. To remove the traction force, user 11 twists grips 77 in the opposite direction to cause motors 65 to operate in reverse and rotate load frame 67 toward the head of user 11.

FIG. 8 shows force values derived from the kinematics of device 63. For example, a longitudinal force of 332 lbs at crossbar 75 (166 lb for each leg pad 57) results in a spinal traction force of 290 lb, as shown at 79. To minimize the chance that user 11 could cause injury by applying excessive force while operating motors 65, it is preferred that a load-limiting device, such as a slip clutch or other torque-limiting device, is installed at hinge 49.

Figure 9:
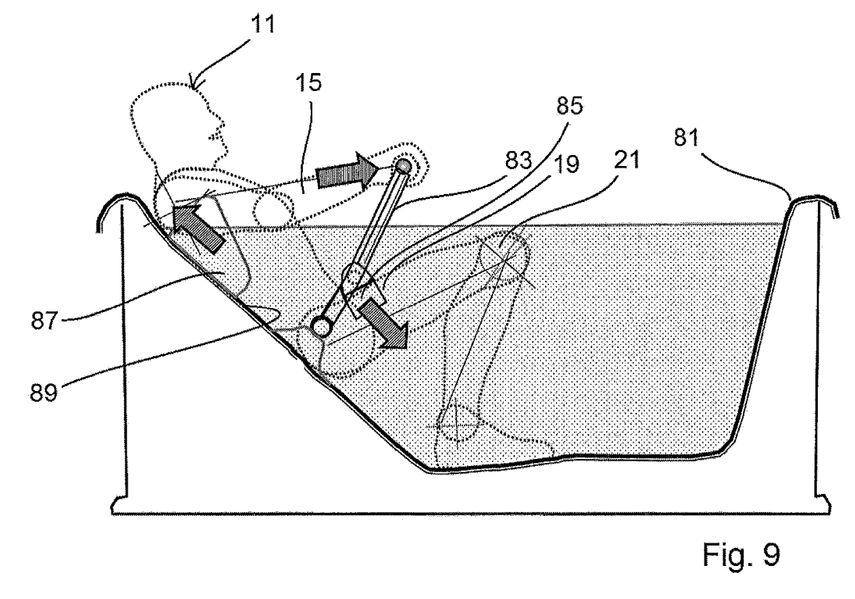
FIG. 9 is a schematic side view of an alternative embodiment of the apparatus of FIG. 2.
Figure 10:
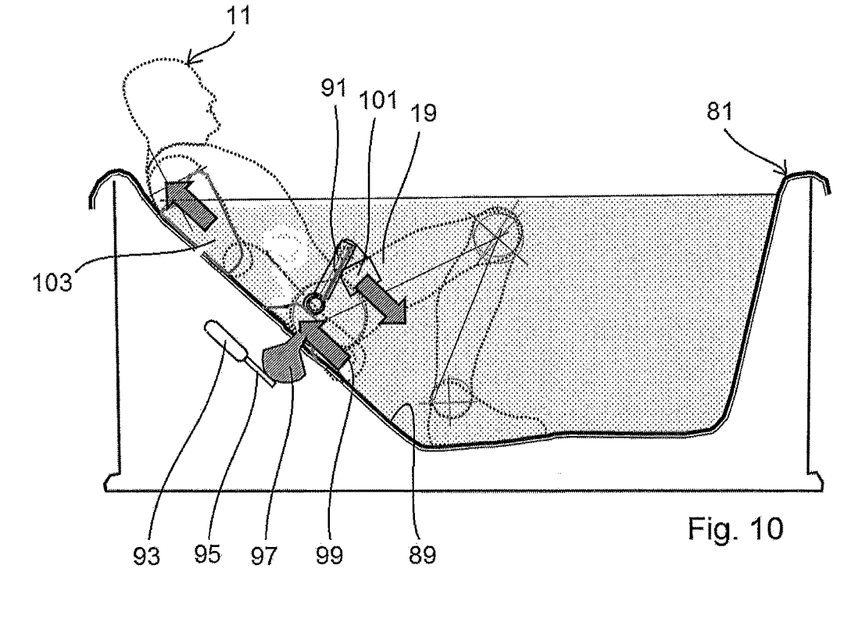
FIG. 10 is a schematic side view of an alternative embodiment of the apparatus of FIG. 6.

In order to allow user 11 to take advantage of the soothing and relaxing effects of warm water during application of spinal traction force, the same basic leveraging principles described above can also be integrated into the design of spas and hot tubs. FIGS. 9 and 10 show a typical spa or hot tub 81 designed to incorporate (or allow installation of) removable components similar to those of devices 29, 63, as described above. These components enable user 11 to apply spinal traction when immersed in a body of warm water. FIG. 9 shows a manually operated lever 83, which is operated by arms 15 to apply force through leg pads 85 to proximal portion 19 of legs 21. Lever 83 is rotatably mounted to hot tub 81. The force applied to legs 21 is reacted by members 87, which are mounted to an interior surface 89 of hot tub 81 and engage the armpits of user 11. This tends to elongate the spine of user 11. Likewise, FIG. 10 shows an electrically operated lever 91, which is rotatably mounted to hot tub 81 and rotated by operation of motor 93. Each motor 93 rotates a corresponding drive screw 95, which rotates a corresponding quadrant 97. Motors 93 are operated by user 11 with grips 99 to apply force through leg pads 101 to proximal portion 19 of legs 21. The force applied to legs 21 is reacted by members 103, which are mounted to interior surface 89 of hot tub 81 and engage the armpits of user 11. This tends to elongate the spine of user 11.

It will be evident to those skilled in the art that the same spine-elongation effect may be achieved by embodiments that affix the proximal portions 19 of legs 21, such as with a stationary crossbar, and extend adjustment sliders 41 toward the head of user 11. Also, embodiments may incorporate a system that both moves a load frame against legs 21 and extends adjustment sliders 41.

The present application provides several significant advantages, including: (1) providing a portable device for applying spinal traction force at higher force levels than previously achievable; and (2) providing a manually operated device that allows a user to multiply the force applied by the user's arms.

The particular embodiments disclosed above are illustrative only, as the application may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

What is claimed is:

1. An apparatus for applying traction force to a spine of a user, the apparatus comprising:
    an elongated chassis having a longitudinal axis and an upper surface adapted to conform to a back of the user whereby the spine of the user extends generally parallel to the longitudinal axis;
    two members extending from the chassis, the two members being located on opposing sides of the longitudinal axis, each member being positioned and adapted to engage an armpit of the user when the user is located adjacent the upper surface;
    a lever pivotally attached to the chassis for rotation about a lateral axis perpendicular to the longitudinal axis;
    a pad coupled to the lever and adapted for contacting a proximal portion of each upper leg of the user when the leg is bent forward at a hip joint; and
    a locking mechanism operably associated with the chassis that locks the lever in place;
    wherein a proportion of a force applied to the lever by the user is applied through the pad to the proximal portion of each upper leg, and opposing forces from the lever acting through a rotational axis of the lever are transmitted by the two members to each armpit, thereby applying a decompressing force on the spine.

2. The apparatus of claim 1, wherein the chassis forms an interior surface of a hot tub.

3. The apparatus of claim 2, further comprising:
a motor carried by the chassis; and
a drive screw driven by the motor for actuating the lever.

4. The apparatus of claim 3, wherein the motor is disposed at least partially within the hot tub.

5. The apparatus of claim 3, wherein the drive screw is disposed at least partially within the hot tub.

6. The apparatus of claim 3, wherein the lever is disposed at least partially within the hot tub.

7. The apparatus of claim 1, further comprising:
a load-limiting device that limits the maximum forces applied to the proximal portion of each upper leg and to each armpit.

8. The apparatus of claim 7, wherein the load-limiting device is a torque-limiting device.

9. The apparatus of claim 8, wherein the torque-limiting device is a slip clutch.

10. The apparatus of claim 1, wherein the locking mechanism comprises:
a ratchet pawl and release mechanism.

11. The apparatus of claim 10, wherein the release mechanism is disposed on a handle of the lever.

12. The apparatus of claim 1, further comprising:
a motor operably associated with the lever.

13. The apparatus of claim 12, further comprising:
a drive screw driven by the motor for actuating the lever.

14. The apparatus of claim 1, further comprising:
a hinge operably associated with the lever and the chassis.

15. The apparatus of claim 1, wherein the chassis is configured for use at an incline in a hot tub.

16. The apparatus of claim 1, wherein the lever is angled.

17. An apparatus for applying traction force to a spine of a user, the apparatus comprising:
an elongated chassis having a longitudinal axis and an upper surface configured to conform to the shape of the user;
two members extending from the chassis, the two members being located on opposing sides of the longitudinal axis, each member being positioned and adapted to engage an armpit of the user when the user is located adjacent the upper surface;
a lever pivotally attached to the chassis for rotation about a lateral axis perpendicular to the longitudinal axis; and
a pad coupled to the lever and adapted for contacting a proximal portion of each upper leg of the user when the leg is bent forward at a hip joint;
wherein a proportion of a force applied to the lever by the user is applied through the pad to the proximal portion of each upper leg, and opposing forces from the lever acting through a rotational axis of the lever are transmitted by the two members to each armpit, thereby applying a decompressing force on the spine; and
wherein the chassis forms an interior surface of a hot tub.

18. The apparatus of claim 17, further comprising:
a drive mechanism comprising:
a motor carried by the chassis; and
a drive screw driven by the motor for actuating the lever.

19. The apparatus of claim 18, wherein the drive mechanism is disposed at least partially within the hot tub.

20. The apparatus of claim 17, further comprising:
a locking mechanism operably associated with the chassis that locks the lever in place.

* * * * *